United States Patent [19]
Harte

[11] 3,992,631
[45] Nov. 16, 1976

[54] FLUOROMETRIC SYSTEM, METHOD AND TEST ARTICLE

[75] Inventor: Richard A. Harte, Redwood City, Calif.

[73] Assignee: International Diagnostic Technology, Inc., Santa Clara, Calif.

[22] Filed: Feb. 27, 1975

[21] Appl. No.: 553,582

Related U.S. Application Data

[63] Continuation-in-part of Ser. No. 447,574, March 4, 1974, abandoned.

[52] U.S. Cl. .............................. 250/365; 250/302; 250/373; 424/12
[51] Int. Cl.² ...................... A61K 39/00; G01T 1/20
[58] Field of Search .......... 250/365, 373, 372, 461, 250/461 B, 302; 424/7, 12, 8; 356/96 B

[56] References Cited
UNITED STATES PATENTS

| | | | |
|---|---|---|---|
| 3,074,853 | 1/1963 | Brewer | 424/12 |
| 3,449,488 | 6/1969 | Bozicevich | 424/12 |
| 3,449,571 | 6/1969 | Hoerman et al. | 250/461 B |
| 3,473,027 | 10/1969 | Freeman et al. | 250/365 |
| 3,666,421 | 5/1972 | Price | 424/12 |
| 3,770,383 | 11/1973 | Price | 424/12 |
| 3,806,256 | 4/1974 | Ishak | 350/96 B |
| 3,826,619 | 7/1974 | Bratu et al. | 424/12 |
| 3,831,137 | 8/1974 | Cuomo | 350/96 B |
| 3,916,205 | 10/1975 | Kleinerman | 250/461 B |
| 3,918,812 | 11/1975 | Holm | 250/461 B |
| 3,941,876 | 3/1976 | Marinkovich | 424/8 |

Primary Examiner—Harold A. Dixon
Attorney, Agent, or Firm—Flehr, Hohbach, Test, Albritton & Herbert

[57] ABSTRACT

A fluorometric system to determine the kind and amount of substances derived from a biological fluid (e.g., serum or urine) or tissue. The substances to be detected (e.g., antigen, antibody, hormone or enzyme) is coated onto a substrate in fluorescent form. Multiple coating areas of different samples may be employed. The fluorometric system includes a source of light to excite fluorescence, a fiber optic cable to conduct the excitation light to such coating, and a second fiber optic cable to conduct emitted fluorescence to a detector device. The system minimizes any gap distance in the path from the sample to the detector which permits the loss of excessive fluorescence. A branched fiber optical cable with the main trunk terminating adjacent the sample with one branch for transmitting light to the sample and the other for transmitting fluorescence light to the detector.

8 Claims, 10 Drawing Figures

FIG.6
FIG.5
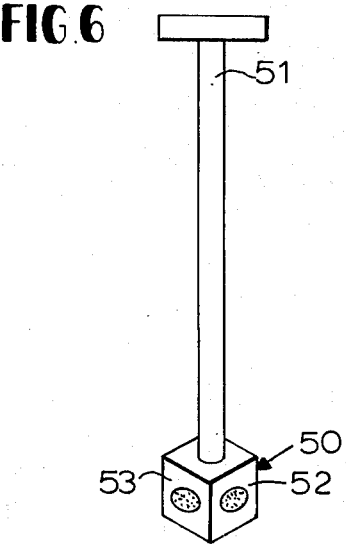
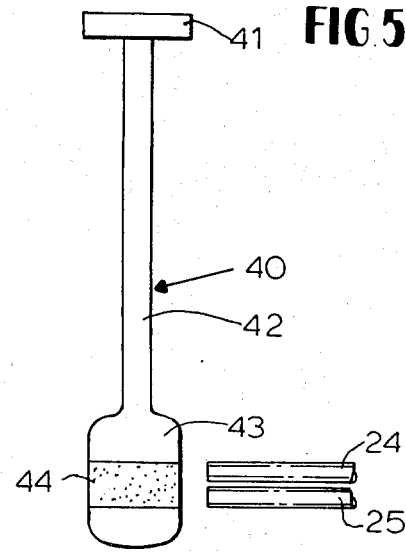
FIG.7
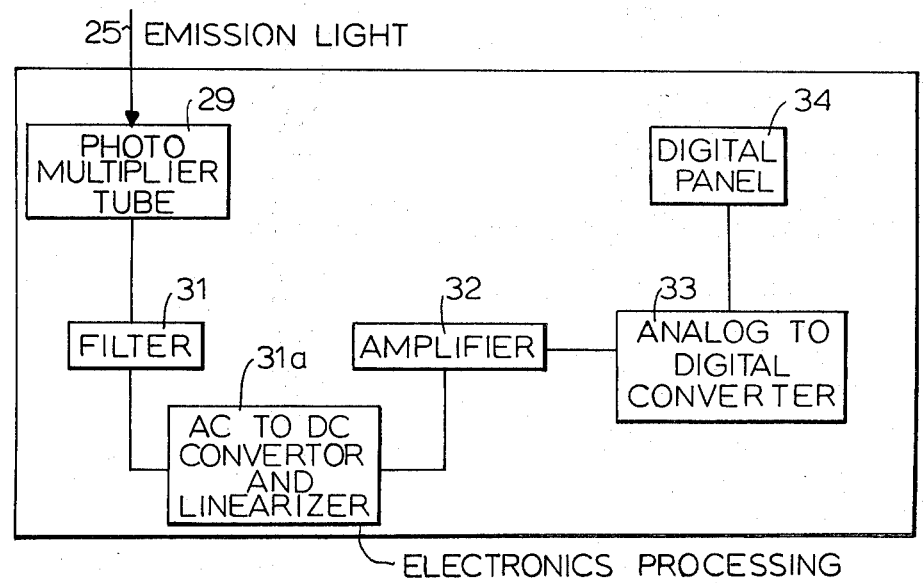

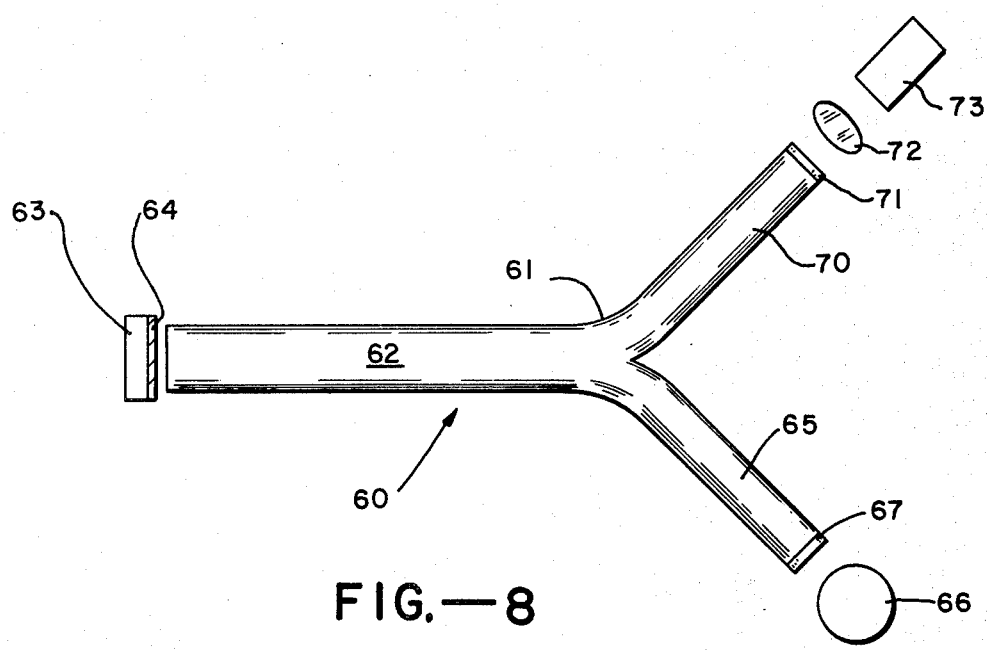
FIG.—8
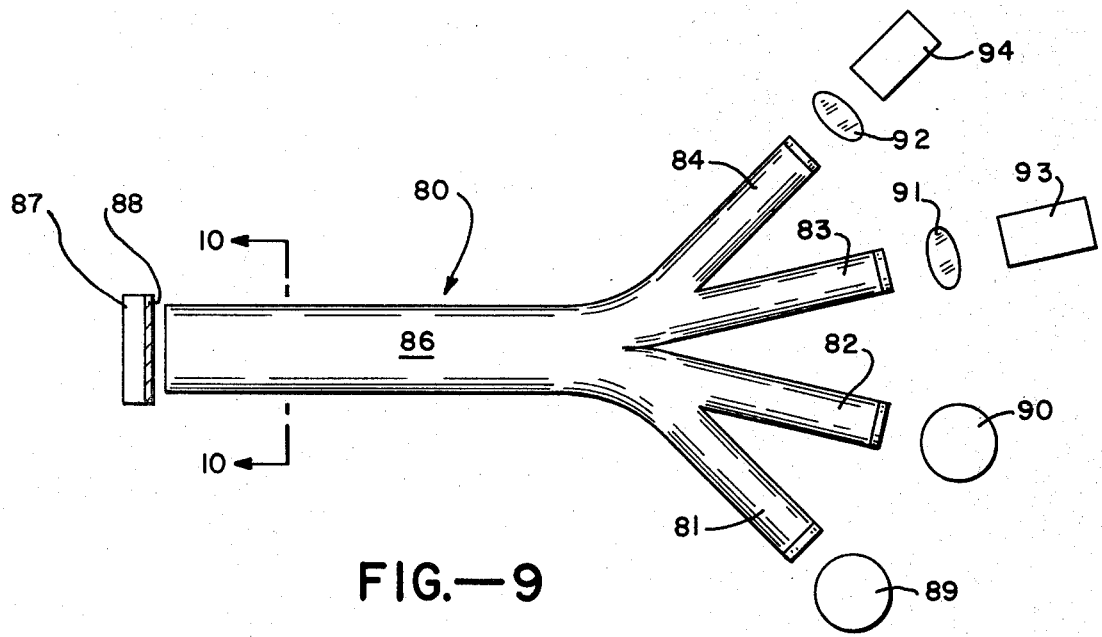
FIG.—9
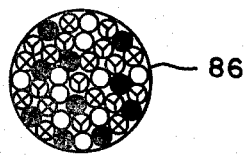
FIG.—10

FLUOROMETRIC SYSTEM, METHOD AND TEST ARTICLE

CROSS-REFERENCE TO RELATED APPLICATION

This application is a continuation-in-part of application, Ser. No. 447,574, filed Mar. 4, 1974 now abandoned.

BACKGROUND OF THE INVENTION

This application relates to the detection of substances derived from biological fluids or tissue tagged with fluorochromes. It detects antigens, antibodies, hormones, enzymes, drugs and other substances.

Most infectious diseases of bacterial or viral nature produce antibodies in the blood serum of the subject. This provides a degree of immunity against future assaults by the identical infectious agent or antigen. One method for detecting the presence of a particular antigen is to add to it a specific antibody which binds to the antigen. If the antibody has been previously tagged with a radioactive element (RIA technique) or a fluorescent dye, which does not interfere with its immunological properties, the coupled complex can be detected by an appropriate detector and, in the case of the fluorescent additive, can be at best semiquantitatively measured, measuring being done in almost all cases in the prior art on a microscope slide for visual inspection.

As noted, testing which relies on fluorescence techniques, as heretofore known, involves qualitative assay, or at best, semiquantitative assay. For example, most fluorescence techniques occur on a microscope slide, and the detector is the eye of a laboratory technician who records the degree of fluorescence as 0, +1, +2, +3, or +4. In some instances, where blood titre or concentration of antibodies is desired, the technician prepares a number of slides; on each is a different concentration of the test material. Thus, the technician may estimate a +4 reaction in the microscope when the blood serum or the bacteria broth medium was diluted 1:4 in distilled water, or 1:16, or 1:128, etc. It would be of great advantage to medical and clinical authorities if a fluorometer could automatically and quantitatively read titre quickly and accurately, without the necessity of making serial dilutions.

Conventional fluorometers are designed for liquid systems and not capable of detecting fluorescently tagged substances derived from biological fluids or tissues on solid surfaces. One reason for this deficiency is the excessive loss (e.g., substantially over 99%) of emitted fluorescent light between the fluorescent substance and that portion of the detector which converts the light into an electrical signal.

There are many reasons why RIA is not completely satisfactory. For one thing, the presence of small quantities of antigen means few counts per second. Since the "noise" of the system is the square root of the signal count, large errors in accuracy are made at these low signal levels. Furthermore, radioisotopes have a limited shelf life due to half life decay, and require special licensing, handling and disposal.

SUMMARY OF THE INVENTION

This invention relates to the testing of a sample substance derived from a biological fluid or tissue which emits fluorescence. In particular, it relates to a fluorometric system and method for the detection of such substances.

The fluorometric system of the present invention measures the sample coated on a solid substrate. It includes a source of light to excite fluorescence in the substrate and light-conducting means for conducting light from the source to the sample. A detector means determines the intensity of fluorescence emitted from the substance and indicates determination. The detector means includes conventional means for converting the light intensity to an electrical signal. Fluorescent light is conveyed from the sample to the conversion means by suitable light-conducting means terminating adjacent the sample. This terminus is termed herein the "light input end" of the detector. The distance between the sample and electrical conversion means defines a light path which is free of any gap distances which permit excessive loss of fluorescence (i.e., a cumulative loss of greater than 95%) available for transmission along the path. Thus, where lightconducting means such as fiber optical cables transmit the fluorescence from the sample to the conversion means, no gap distance at either end of the cable exceeds this level.

The coated substrate to be viewed in the fluorometer may comprise a single sample coating on a body. Alternatively, a body adapted to enable detection and determination of more than one sample substance may include multiple spaced coating areas (e.g., bands) of different substances. A single coated area may include different substances in random dispersion tagged with different fluorochromes.

A particularly effective fluorometric system includes a branched fiber optical cable for conducting light from the source to the sample and for conducting emitted fluorescent light from the sample to the detector. One branch conducts light from the source to the sample and the other conducts the fluorescent light to the detector. These branches meet in a common fiber bundle terminating at the light input end. In this manner, the area of coincident excitation and emission is maximized at extremely close gap distances.

Another advantageous fiber optical system includes at least two fiber optical cables for conducting the emitted light to the detector and means for alternating the input to the detector between the cables. This system can read at least two coated areas on a single substrate without movement of the substrate as in a comparison between a standard quantity of sample and one or more unknown samples. Similarly, both the light conducting means to excite fluorescence and to receive fluorescence may comprise branched optical cables for transmitting multiple wavelengths of light to the sample and receiving different fluorescent signals.

BRIEF DESCRIPTION OF THE DRAWINGS

The invention and some modes of carrying it out will be explained and illustrated by the following specific description and by the annexed drawings, wherein In the drawings:

FIG. 5 is a schematic perspective view of another embodiment of the article and the device of this invention, comprising a flat plate with a handle.

FIG. 6 is a similar view of a further embodiment employing a cube with a handle, for multi-test purposes.

FIG. 7 shows one embodiment of the detector devices of FIGS. 1 and 3.

FIG. 8 and 9 are schematic views like FIG. 1 of modified forms of a fluorometer.

FIG. 10 is a cross-sectional view of the common fiber optical cable of FIG. 9 taken along the line 10—10.

DETAILED DESCRIPTION OF THE PREFERRED EMBODIMENTS

The present invention relates to a fluorometric system and method to quantitatively detect and measure a fluorescent sample substance coated in a layer on a substrate. As defined herein, the term "fluorescent sample substance" is one which includes a material derived from either a biological fluid or tissue and which, along or in combination with other materials, emits fluorescence upon excitation with a selected wavelength of light in a solid layer form. Common fluorescent sample substances include autofluorogenic material derived from a biological fluid (e.g., tetracycline), materials derived from such fluids tagged with fluorochrome before or after isolation, materials derived from such fluids linked in the layer with homologous fluorochrome-tagged materials (e.g., antigen or antibody, one of which has been tagged with a fluorochrome).

The present description will make particular reference to the last named substance.

Figure 1:
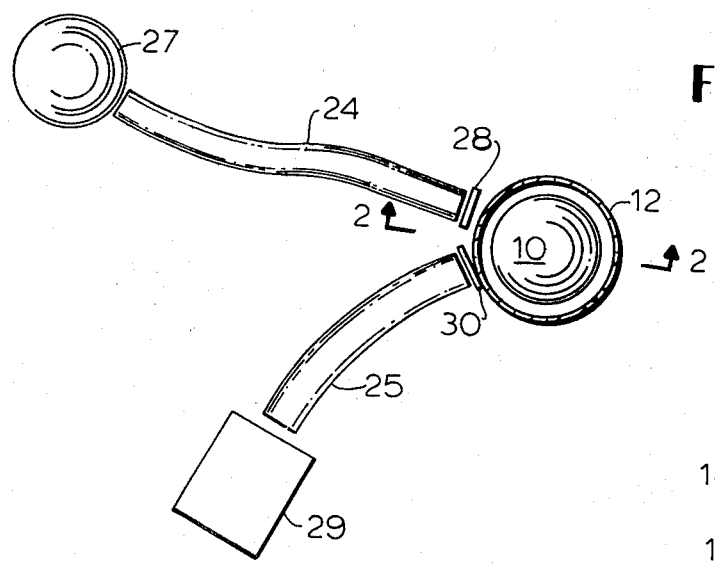
FIG. 1 is a top, schematic view of one embodiment of the invention, the cuvette being without its cap.
Figure 2:
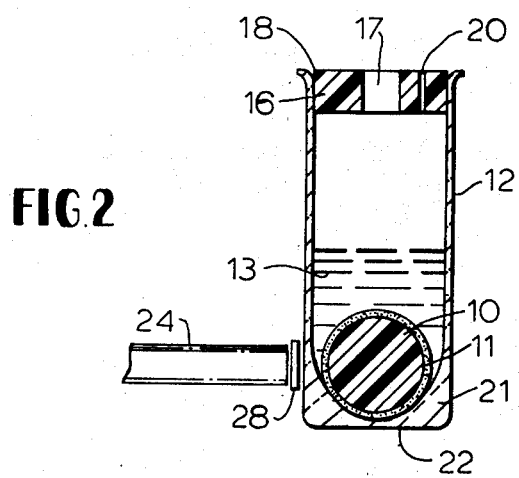
FIG. 2 is a partial sectional, elevational view taken on line 2—2 of FIG. 1.
Figure 4:
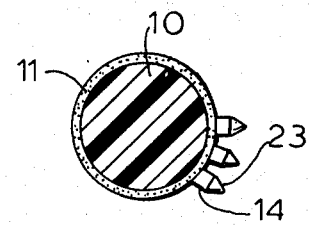
FIG. 4 is a schematic sectional view of a solid body coated with antibody having antigen and fluorescing antibody attached according to one feature of the invention, the relative size and thicknesses being exaggerated for purposes of illustration.

In the embodiment of the invention shown in FIGS. 1, 2 and 4, as one example, there is provided a ball 10, typically of plastic, e.g., nylon, which bears a dried film or coating 11 of an antibody to the antigen to be determined, e.g. to Australian antigen. Since coating of all balls will be done at substantially the same temperature of 37° C, and for substantially the same incubation period, e.g., 30 minutes, each ball will have substantially the same amount of antibody on it, which is important for quantitative results. In a ball 10 such as shown in FIG. 4, the total surface area is 314 mm² where the diameter is 10 mm. Whatever plastic is used, the ball or body 10 is not a microbody and is typically on the order of 5-20 mm in diameter so that an area at least one square mm is viewed by the fluorometer. The ball is dropped into a cuvette 12, in this instance of 12 mm diameter. If fluorescence is to be detected and measured with the ball in the cuvette, the cuvette should be formed of a material, e.g., glass, which is nonfluorescing at the wavelength to be measured and which prevents transmission of greater than 30% of the fluorescent light. One ml of serum 13 from a patient or subject is added to cover the ball 10, and the cuvette gently rocked for 5 minutes of room temperature incubation. Australian antigen 14, if present, binds to the antibody 11 on the ball 10. A cap 16 with a 5mm hole 17 is placed on the open end 18 of the cuvette 12 and the cuvette 13 is inverted, permitting the serum to run out. A small second hole 20 to permit passage of air is also provided in the cap 16. Suitably, the cuvette 12 has a rounded or generally hemispherical inner surface 21 at its base 22, whereby the ball 10 is held in position and does not roll around during the fluorescence test, where a ball is used and fluorescence is measured in cuvette 12.

After incubation with the subject serum, the cuvette is rinsed out, e.g., with aqueous phosphate buffer or distilled water, which is then also allowed to pour out of the 5 mm hole 17, the 10 mm ball 10 remaining in the cuvette 12. Then there is added to the cuvette 1 ml of antibody solution tagged with a substance which fluoresces under ultraviolet light. Such a fluorescent tag or label substance can be, e.g., sodium fluorescein isothiocyanate or other suitable substance. However, sodium fluorescein isothiocyanate, with excitation at 460 nanometers and emission at 520 nanometers, is advantageous. The material in the cuvette 12 is again incubated as decribed above, the liquid poured off through the hole 17 and the cuvette and bead rinsed as before. The ball 10 now bears the antigen 14 and attached fluorescent antibody 23 where Australian antigen is present. The cuvette 12 and body 10 are now ready for insertion into the fluorometer system.

In the fluorometer system, the cuvette 12 is so placed that a fiber optical cable 24 conducts ultraviolet light from a light source 27, which can be any desired source; the light then passes through a gelatin filter 28 which ensures that only light of the exciting wavelength reaches the bead or body, then through the wall of the cuvette 12 and strikes the coated surface of the body 10 whereupon it excites fluorescence of the coupled complex 23. A second fiber optic cable 25 is disposed preferably at a small angle, less than 30°, from the cable 24; and the emitted fluorescence passes through a gelatin filter 30, which ensures that only emitted fluorescence reaches a photomultiplier 29 via the fiber optic cable 25. The photomultiplier tube 29 transduces the intensity of the emitted fluorescent light to an electronic signal. This signal goes to a filter 31, a processor 31a (which converts the AC signal to a DC signal, e.g., through a peak-to-peak detector and linearizes the relationship between fluorescent light intensity and DC voltage, as by a four-step diode linearizer), amplifier 32, an analog-to-digital converter 33 and then is displayed on a digital panel meter 34 as calibrated directly into titre (FIG. 6).

Figure 3:
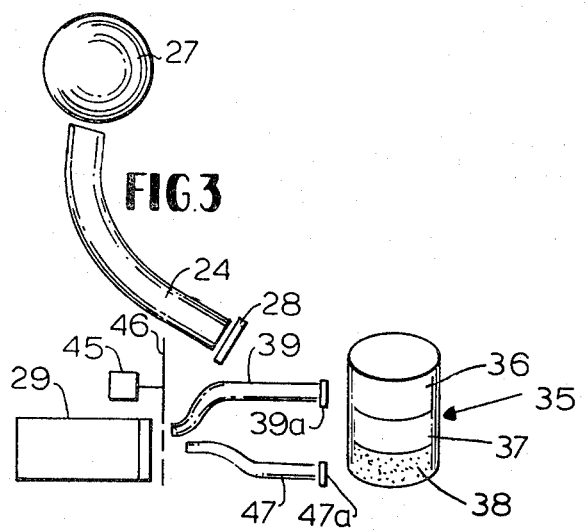
FIG. 3 is a schematic view of another embodiment of the invention wherein the solid body is a cylinder.

In the embodiment shown in FIG. 3, a nylon cylinder 35 is employed instead of the ball 10. The upper portion of the cylinder 35 is, in this instance, coated with a standard fluorescent coating 36, i.e., of the same fluorescent substance as is used to tag the antibody coating 38 of the lower portion of the cylinder 35 and has a known titre as measured on the detector device which is employed in the test or assay; in this instance, the fluorometer described herein. Suitably a blank space 37 is left around the surface of cylinder 35, separating the upper and lower coatings, 36 and 38, respectively. The lower coating 38 may contain streptococcal fluorescent-tagged antibody, being prepared in the same manner as described above with respect to the body 10, except that only the lower portion is immersed in the body liquid, to determine if any of the suspected antigen or antibody is present in the serum being tested. In this embodiment, the ultraviolet light source 27, the fiber optical cable 24 and the filter 28 are again provided. Two fiber optic cables 39 and 47 are provided with respective filters 39a and 47a. One such cable 39 conducts fluorescent light from the standard fluorescent coating to the photomultiplier tube 29, and the other such cable 47 conducts emitted fluorescence from the lower coating 38 to the photomultiplier tube 29. A chopper wheel 46 operated by a motor 45 revolves and alternates the flow of light from each coating 36 and 38 to the tube 29. In this manner, a direct comparison is obtained between the standard and the test portions.

In the embodiment of FIG. 5, the cuvette 12 contains a paddle-shaped body 40 having a handle 41 at one end, a stem 42 and a wide, flat head 43 at the other end, the head 43 bearing a coating 44 of sample. In this embodiment, the two fiber optic cables 24 (fog excitation light) and 25 (for emitted fluorescent light) are parallel to each other, or at an angle of 0° with respect to each other. Conveniently, the two cables 24 and 25 can also be arranged as a coaxial cable. The other elements of the device and system are as previously described and shown.

Another embodiment, a multiple test body, is shown in FIG. 6. Here, the body is a cube 50 at the end of a handle 51. The cube 50 can present four faces, two faces 52 and 53 being visible. Each face has a differnt sample. Four different fluorescent tags can be provided, and the fluorometer may have a filter wheel with four selected wavelength regions to isolate energy going to the photomultiplier tube 29.

As the operator rotates the tube 50 (or other multi-faceted polyhedron body), each test can be read in sequence. A handle can similarly be attached to a cylinder, sphere, or other substrate. Other means of moving the substrate upon which different biologically- derived substances are layered may be employed to vary the surface exposed to the fiber optical cable.

Broadly stated, the banded cylinder of FIG. 3 and the cube FIG. 6 constitute two forms of the use of multiple areas coated on a substrate body adapted for rapid multiple fluorometric detection determination. Any shape of substrate may be employed so long as it includes a first area of fluorochrome-tagged sample substrate and at least one other area of fluorochrome-tagged substance. Such different areas may include a standard area of predetermined quantity of the same type of substance as the fluorochrome-tagged substance. In this manner, the two different areas, such as bands 36 and 38 of FIG. 3, may be viewed to provide a direct comparison between the intensities of the standard and test portions.

One technique for accomplishing the above multiple determination is by the use of multiple fiber optic cables in combination with a chopper wheel using the same photomultiplier tube. Alternatively, duplicate photomultiplier tubes and fiber optic cables may be employed without the use of the chopper wheel. Instead of using the above substrate for detection of fluorochrome-tagged specimens against standard ones, different test specimens of the same or different type may be deposited on a single sample substrate holder or body in spaced apart areas. The wavelength of light which excites fluorescence may also be varied to the different areas as set forth below.

FIG. 8 shows a modified form of fluorometer 60 in which a single branched fiber optic cable 61 replaces the two separate cables 24 and 25. A single-bundle portion 62 of the cable 61 leads to and away from a solid base 63 having a fluorescent surface 64. One branch 65 of the cable 61 transmits light from a lamp 66 or other light source and a suitable ("blue") filter 67 to the fluorescent surface 64. A second branch 70 of the same cable 61 conducts the emitted fluorescence from the surface 64 to a suitable ("green") filter 71 and thence through a lens 72 to a solid state or photomultiplier type of detector 73. Operation is basically the same as in FIG. 1 with readily apparent differences.

FIG. 9 shows another modified form of fluorometer 80 in which branches 65 and 70 of fiber optic cable 61 replaced with branch fiber optic cables 81, 82, 83, and 84, respectively. A single-bundle portion 86 of the cable leads to and away from a single base 87 having a fluorescent surface 88. Branches 81 and 82 transmit light from lamps 89 and 90, respectively, or other light sources, to fluorescent surfaces 88. Branches 83 and 84 of the same cable 86 conduct the emitted fluorescent from the surface 88 through suitable lenses 91, 92, respectively, to solid state or photomultiplier type of detector 93 and 94, respectively.

One method for employing the device of FIG. 9 which is highly advantageous is to view surface 88 which includes a plurality of biologically derived substances in random dispersion. Each of the substances is tagged with a fluorochrome which emits fluorescence responsive to a different wavelength of light. Thus, lamps 89 and 90 emit the different fluorescence exciting wavelengths while the multiple fluorescence is received simultaneously by detectors 93 and 94 through light conducting branches 83 and 84, respectively. The multiple fluorochrome tagged substances in random dispersion may also be read using the single branched fiber optical cable of FIG. 8. In this instance, a single lamp or other lamp source replaces lamps 89 and 90 and a plurality of filters are employed to provide the proper wavelengths to excite the respective fluorochromes in the samples. Similarly, light-conducting cables 83 and 84 may be replaced with a single cable and detectors 93 and 94 may be replaced with a single detector so long as the wavelengths to which the detector is responsive is synchronized to the selected fluorochrome to be excited.

An important feature of the present fluorometric system is the maximization of fluorescent light which is received from the sample. This is particularly important when the fluorescent substance is present at very low concentrations. it has been discovered that this objective is accomplished by avoiding gap distances in the light path between the fluorescent substance and the means for converting the light intensity into an electrical signal for quantitative measurement. With a fiber optic cable conducting light from the light input end adjacent the sample to the conversion means, such gaps include the distance between the light input end and the sample substance and any distance between the optical cable and conversion means.

It has been found that for average fluorescence intensity, at a minimum, the cumulative fluorescence loss across all of such gap distances in the above light path should not be greater than 95% of the fluorescence available for transmission along that path. Such losses do not include losses due to viewing only a portion of a fluorescent sample surface. To take this into account, such loss is related only to the fluorescent light emitted from the sample within an area defined by the light input end perimeter projected onto the sample surface. Although limiting the gap loss in fluorescence to 95% across the total light path is a significant improvement over conventional fluorometers, it is preferred to limit such loss to below 50 to 90% and optimally to 10% or less. At such loss levels, even minute quantities of sample may be detected and determined quantitatively.

The above considerations deal primarily with fiber optic cables and light pipes and the importance of their close proximity as expressed by gap distance, to surfaces from which they receive and to which they deliver light. Light conducting systems may also contain such components as lenses to collect and focus light, mirrors to reflect and redirect it, and apertures through which light passes after dispersion. When components such as these receive light from a surface that is radiating it into a hemisphere, the amount of such light they capture is approximately proportional to that portion of $\pi$ steradians defined by the circumference of the area they project on the hemispherical surface generated by a radius equal to the gap distance between the light emitting surface and the component receiving it.

Based upon the above relationship, the circumference which permits loss of no greater than 95 % of emitted fluorescence corresponds to one that will generate a solid angle no less than approximately 0.3 steradian. The solid angle of non-circular cross-section is defined as one generated by an equivalent circular area.

Another technique to avoid loss of fluorescence is to maintain the gap between the sample coating and light input end of the detector free of solid medium which prevents transmission of excessive quantities of fluorescent light. It has been found that glass or certain plastics (e.g., polystyrene) at moderate thicknesses of less than 005 inch causes a loss of fluorescence less than 30%. Although it is preferable to avoid the interposition of such a solid medium, such losses are acceptable if necessary or convenient to the system. For example, in the embodiment schematically illustrted in FIG. 1, it may be convenient to employ a thin walled cuvette to retain a coated substrate of a spherical shape. If so, the cuvette should be formed of a material which does not cause the loss of in excess of 30% of the fluorescence.

Referring to FIG. 10, a cross-sectional view of the common fiber bundle 86 of the branched cable 80 is illustrated schematically in which the fibers of the various branches are enlarged for viewing clarity. Such fibers are schematically represented by a solid circle, an open circle, a circle containing "x" and a circle containing "y". It is apparent that the four different types of fibers in this particular arrangement are randomly dispersed. It may be desirable to accomplish a specific optical effect to arrange them schematically as in concentric circles, not shown, or to use fibers of different diameters.

A study of the fluorometric system illustrates that a significant factor which contributes to this percentage loss is the ratio of the gap distance between the sample and the effective diameter of the light input end of the emitted light receiver. The term "effective diameter" means either the diameter of a light input end of circular cross-section or the equivalent diameter of a non-circular cross-section. This latter term may be approximated by reference to the formula:

$$area: \frac{\pi d^2}{4}$$

The effective diameter, d', of non-circular cross-section is defined as $$\frac{4 \times area}{\pi}$$

Reference to the relationship of gap distance to effective diameter is based upon the approximate relationship that intensity of fluorescence is inversely proportional to the square of the distance from the fluorescent substance. This approximation does not take into account an increase in capture accomplished by minimizing the angle of reflectance, i.e., the angle between the light conducted to the fluorescent substance to excite fluorescence and that received by the light input end of the detector means. It has been found that this value is not as significant as the gap distance. It is apparent that the effective diameter of the light input end is significant since an increase in the area of that surface causes a corresponding increase in light captured.

Using the above calculations, a gap distance adjacent the sample which permits loss of no greater than approximately 95% of emitted fluorescence corresponds to a ratio of gap distance to effective diameter of the light input end of no greater than about 5:1. Similar calculations may be made to determine the theoretical ratio of other fluorescent loss percentages. It should be understood that this ratio is only an approximation. The same formula applies to other gap distances in the light path such as between the fiber optical cable and the portion of the detector which converts the light to an electrical signal and between any lenses and mirrors which may be employed in the light path.

The branched fiber optical system of FIGS. 8–10 is particularly effective in reducing to a minimum the gap distance which can be obtained to minimize loss of emitted fluorescence. This is based upon the principle that the only area of the fluorescent substance which can be received by the detector is where the light transmitted to the substance for exciting fluorescence coincides with the viewing area of the light input end of the detector. This can be accomplished with separate fiber optical cables as in FIG. 1 until a gap distance is reduced to relatively small values. As this reduction occurs, the area of coincidence of totally separate light exciting and light emitting cables continuously reduces. It is apparent that this may be a limiting factor on the gap distance and consequently may cause excessive fluorescence loss for a sample substance in extremely small quantities. On the other hand, the use of branched cables each including a plurality of light transmitting fibers which terminate in a common fiber bundle at the light input end enable the fluorometer to be disposed extremely close to the fluorescent sample without lack of coincidence. The only limit on this is when the gap distance approaches zero at which point the fine fibers of the fiber bundle act like independent cables.

The common fiber bundle is particularly effective in embodiments such as multiple branching of FIG. 9. Cables with separate light input and output ends for each of the branches of cable 80 would require a fairly substantial gap distance to assure a sufficient area of coincidence.

The above description makes reference to fiber optical cables as the preferred light conducting means. It should be understood that other optical conduits such as light pipes and lenses may also be employed in those instances where the distance does not require the use of common fiber optical bundles.

The foregoing description describes the present fluorometric system in terms of certain fluorochrome-tagged biological fluids or tissues. These are employed in the testing of body fluids, such as serum, urine, or other fluids, to ascertain the presence of pahtogens or their toxins or to ascertain concentrations of other substances in the fluid. In general, such fluorescent sample substances fall into the category of pairs of material each of which selectively or sterically fits with a mating substance. Pairs of this type include antigen-antibody, enzyme-substrate, binding protein-hormone, binding protein-vitamin, enzymes-inhibitors, and the like. However, other fluorescent sample substances may be bound to a substrate with pairing as by physical entrapment or sorption.

The system and method of the present invention are applicable to the detection of a wide variety of fluorescent sample substances. They include drugs of abuse such as morphine, methadone, cocaine and barbiturates; drugs used for the control of certain chronic diseases or conditions, such as digoxin (cardiac disorders), insulin (digitalis), and diphenylhydantoin (epilepsy); hormones such as thyroxine and triiodothyroxine; steroid hormones such as aldosterone, cortisol, testosterone, estriol and progesterone; peptide and protein hormones such as adrenocorticotropin, angiotensin, gastrin, chorionic gonadotropin, follicle stimulating hormone, growth hormone, luteinizing hormone, neurophysin, placental lactogen, and thyroid stimulating hormone; vitamins such as cyanocobalamin and folic acid; enzymes such as chymotrypsin, creatine phosphokinase, alkaline phosphatase, and lactic dehydrogenase; antigens such as carcinoembryonic antigen, hepatitis associated antigen and alpha fetoprotein; antibodies such as anti-toxoplasmosis antibody, antithyroid antibodies and anti-nuclear antibodies; cellular formed bodies such as bacteria, fungi, protozoa, erythrocytes and leucocytes; serum proteins such as fibrinogen, anti-hemophilia factors, lipoproteins, immunoglobulins and thyroxine binding globulin; cellular degradation products such s myoglobins, bacterial toxins, and lyzozymal digests, etc. Other substances can be employed so long as they are fluorescent or rendered so as by direct labeling or through binding with fluorescently labeled specific binding proteins, substances, inhibitors, enzymes, antigens or antibodies, and can be attached, either before or after they are directly or indirectly labeled, to a surface by physical adsorption, specific protein binding, immunosorption, substrate or inhibitor binding, physical entrapment in pores of a matrix, ion exchange, or other methods.

An important system of the foregoing type is the antigen-antibody pair. Antigens are generally defined as substances capable of evoking an antibody response. Antigen reactions are meant to refer not just narrowly to an in Vivo antibody production and binding to such substances but also to in Vitro situations in which normally non-antigenic substances can be employed to bind other substances. For example, thyroxine-binding globulin (TBG), a normal constituent of human blood, may be applied as the first layer of a sandwich on a solid surface, to bind thyroxine ($T_4$), another normal constituent of human blood. Thus, the $T_4$-TBG binding is the analog of the antigen-antibody binding, and $T_4$ may be assayed fluorometrically in the fluorometer described herein. Thus, protein binding reactions may be generally treated as the relation between a substance and protein that tends to bind the substance. Also, antibody-antigen reactions serve as important examples of the general case, which also includes the binding of certain drugs, hormones, and enzymes to their substrates, as well as immunological materials, and may be generally understood as including or indicating the generic concept.

In one embodiment described above, a solid layer of fluorochrome-tagged substance (e.g., antigen) is coated on as a film on the exterior surface of a substrate or solid body, for example, a ball, cylinder, or flat plate, which serves as a mobile base. The substance may be a first type of protein (e.g., an antigen), the presence of which is suspected in the serum of the subject or patient or of a second type of substance (such as an antibody to such antigen). The substance may also be a hormone, an enzyme, or some other protein of interest.

A second standard body (a calibration body) having already been exposed at the factory to an antigen solution of known titre, already possesses all three layers and should read a known value on the instrument if it is operating properly, e.g., +4 at a titre of 128. The instrument is adjusted, if necessary, to give the correct calibration.

An immunobody exposed to a patient's serum may then be inserted into the fluorometer, and the titre results are read on the quantitatively calibrted digital meter.

Where the shape is other than a sphere, e.g., a cylinder, flat plate, cube or other suitable geometric form, the above procedure using a plurality of separate areas coated with fluorochrome-tagged substances may be employed. For example, as set forth above. One portion of such body, e.g., a cylinder, or flat plate, can be coated with a standard fluorochrome, as known in the art, which represents a calibration value. The other portion longitudinally of such body can be coated with antigen, fluorescent antibody, etc., for testing in the same manner as the spherical immunobody. A fiber optic cable goes to each of the two portions of the cylinder to read first the internal calibration, then the test results. By using a "chopper" wheel or rotating sector disc, or electronic switching, the signals to the photomultiplier tubes are alternated. This use of an internal standard reduces the steps otherwise required in removing a test cuvette and replacing it with a standard cuvette. Where a solution of the antibody or antigen is employed, the concentrations are those well known in this art. For instance, in testing for staphylococcus the titre can be 1:128, for gonorrhea, 1:8, and so on.

One standard technique for binding sample substances to the substrate is called by immunologists the "Sandwich Technique". In this case, an antibody to the specific disease whose presence is being determined, is coated to the substrate. Many plastics have the property of being able to bind complex proteins directly, of which antibodies are one type. A typical case uses the test for "Australian Antigen" in the blood which is regarded as prima facie evidence of hepatitis infection. The antiAustralian antigen-antibody is bound in a film to the plastic substrate. The serum of the subject suspected of carrying the antigen is coated on the antibody film. If the antigen is present, it binds immunologically to the antibody film. After a rinse with water to remove all unbound material, more antibody with a fluorosecent tag is added. It binds to the antigen if it is present. Then a final rinse removes all unbound fluorescent tagged antibody. The fluorescence, if any, emitted from the coating is detected by the present fluorometric system.

In addition, to the "sandwich" technique described above, other standard immunofluorescent techniques can be employed, e.g., the indirect technique. In an example, the body is coated with antigen — a preparation of treponema pallidum, for instance, if it is desired to determine antibodies for syphilis in the subject. The serum of the subject is incubated with the body, then rinsed. Then fluorescent-tagged antihuman antibodies (harvested from goat or rabbit) are added, incubated and rinsed. If human antibody for treponemae was present in the serum, then it adhered to the body by immunoreaction and, in turn, captured by the fluorescent antibodies from the goat, for example, hence, a quantitative reading of titre for syphilis can be obtained. This is a modification of the standard accepted FTA-ABS Test (fluorescent treponemal antibody-absorption) whereby the body system and immunofluorometer of this invention enable accurate quantitation.

Any infectious disease producing antibodies would be amenable to assay by this technique and includes such diseases of public health interest as: syphilis, gonorrhea, "strep" throat infection, dysentry, salmonella infection, typhoid, rabies, serum hepatitis, influenza types, etc. This invention can also be useful in quality control in the food and pharmaceutical industries.

Also, as another application employing the predescribed techniques, it is often of value not only to diagnose the presence of disease (antigens) but determine the body's protective immunity to disease (antibody titre) as a result of dilberate innoculation or vaccination. As an example, a physician innoculates a child with D.P.T. serum to provide immunity to diptheria toxin, pertusin or whooping cough and tetanus. He then assumes that all 3 have "taken". A test of the serum for antibody for each would, in fact, determine if all 3 antigens were effective in creating sufficient immunizing antibodies. Present technology does not allow this simple screening procedure.

Illustrations of the system of this invention where antigens or antibodies in the strict sense are not involved but where protein-binding procedures are still employed include the following combinations:
1. Thyroxine (T$_4$) with thyroxine-binding globulin (TBG)
2. Thyroxine (T$_4$) with thyroxine-binding pre-albumin (TBPA)
3. Intrinsic factor with vitamin B-12
4. Insulin with alpha-2-macroglobulin
5. Cortisol with trans cortin
6. Haptoglobin with hemoglobin In all cases, one of the pair (a first type of protein) may be bound to a solid substance and may also bind with and remove from blood serum the other member of the pair (a second type of protein capable of binding to the first type), which can then be exposed to fluorochrome-tagged molecules of the first type. These examples and the generalized use are strictly analagous to the antibody-serum antigen-tagged antibody systems described in several of the immunological reactions.

Other variations include the use of other fluorescent tags such as lissamine-rhodamine B, D.A.N.S. (1-dimethyl-aminonaphthalene-5-sulfonic acid) orthophthaladehyde, and fluoroescamine, which are frequently used in fluoroescence microscopy. The first two possess an orange or red emission spectra rather than the yellow green or fluorescein and the second two possess a blue or green emission spectra. The only variation in the fluorometer here described, would be the change in exciation and emission filters used, as well as the change in the fluorescent tag on the antibodies in the reagent kit.

Another important varition might be termed microanalysis by the fluorometer. Here, instead of large fiber optic bundles, very small diameter bundles, e.g., less than 10 ml (0.010 inch) or even single fibers are used to carry light to and from a microcuvette like a capillary tube. Here a microball of small diameter (for example, 50 to 100 microns) is coated with the antibody for the test in question. The reason for this scaling down of cuvette and reagent ball size, is to permit an immunofluorescence assay of a microsample of blood serum. This would be very attractive in any mass screening program where finger puncture blood is so much easier to obtain than a venous puncture of the arm. It enables the mass screening of infants for pediatric testing of diseases of the newborn or the very young, etc.

There are cases in which it is desirable to determine the presence of more than one microorganism. For example, symptoms which may bring a patient to a urologist might suggest kidney, urethral, or bladder infection. Ordinarily microbiological plating of the urine specimen on a number of different growth media, and subsequent 24 to 48-hour incubation is required to determine which, if any, microorganisms are responsible. Furthermore, different organisms require different antibiotic treatment.

When the fluorometer is equipped with a filter wheel so that several different wavelengths can be selected for several particular fluorescent tags, e.g., 1. fluoroscein isothyiocyanate (yellow-green); 2. lissamine rhodamine B-200 (deep orange); 3. D.A.N.S. (1-dimethylaminonaphthalene--sulfonic acid; red); 4. ortho-phthaldehyde (blue-green); and 5. fluorescamine (blue-green) and when each tag is attached to a different antibody for three microorganisms of interest in urinary tract infections (E. Coli, Pseudomonas, and staphylococcus), then one, two or all three may be simultaneously determined and identified. In the event of multiple determinations, it may be convenient to prepare the test bodies with multiple separate bands of sample as described elsewhere herein with reference to a single determination. The standard band can also be included or can be omitted, if desired. Alternatively, the body can be prepared with a coating of a mixture of several samples.

It is also possible to incubate a single body in a mixture of antibodies for the several organisms, and if all are present in equal concentrations, there should be enough binding sites on the polymer chains of the plastic to take about equal amounts of each antibody.

The coated substrate of this invention should be distinguished from microbeads and the like. It should have an area at least 1 mm. If a ball or cylinder, it is preferably no larger than 5–20 mm in diameter; if a flat plate or cube, it should be preferably no wider than 20 mm. The 1 mm minimum area presents a macroscopic surface to the detector and enables integration of fluorescent light from large aggregates of tagged molecules and thereby reduces sampling errors from sample to sample.

The present specification has been described in terms of the use of polymeric (plastic) substrates to bind the test sample substances. Such polymeric substances include polymethylmethacrylate, polystyrene, polyamides (nylon) or any other conventional polymer capable of binding the substances by physical adsorption of protein.

Other substrates which are capable of binding the test substance, either directly or with the aid of an intermediate protein bond, include such classic adsorbents as activated charcoal, silica, alumina, ion exchange resins, or dextran. Proteins are also immobilized by physical adsorption onto materials as reported in Science News, May 18, 1974, paee 324. Also, a considerable technology has developed for immobilizing proteins that can serve as the coated layer of the substrate. For example, techniques for immobilizing enzymes as reported in a 1973 book by Zaborsky entitled *Immobilized Enzymes*, published by The Chemical Rubber Company, Cleveland, Ohio, and proteins such as antibodies and antigens as reported by Campbell and Weliky in Volume 1 of Methods in Immunology and Immunochemistry, (42) published by Academic Press, New York, NY, are suitable for this purpose. As these authors point out, strong attachment of proteins and other substances such as enzyme substrates and inhibitors may be achieved by entrapment in the pores of an expanded substrate matrix, by covalent linkage to the chemical sites on the substrate, or by chemical fixing of physically adsorbed substances coating the substrate with agents such as glutaraldehyde. Covalent linkage may also be made with ceramic substrates such as glass, as described by Weetal in U.S. Pat. No. 3,652,761. Other substrates (e.g., metals) prepared by these or other conventional techniques in which where a surface attachment of the test substance can be accomplished, are suitable.

The first three examples show the steps which can be practiced in carrying out the present invention by three varying techniques, reading the test results on the device described herein. In each instance, the object is to determine the presence and amount of gonorrhea infection:

Example 1. The Sandwich Technique for Gonorrhea
Steps:
1. Insert a 10 mm diameter nylon ball covered with gonorrhea antibody into the cuvette.
2. Add patient's blood serum, enough to cover the ball. Incubate at room temperature for 5 minutes, pour off liquid.
3. Add fluorescent gonorrhea antibody solution — sufficient to cover ball. Incubate at room temperature for 5 minutes, pour off liquid.
4. Rinse well with buffer solution, then pour off.
5. Drop the cuvette into the fluorometer and read the titre. When antigen is present in the subject's serum, indicating a present gonorrhea infection, the meter reads "+" and at a definite titre concentration.

Example 2. The Sandwich Technique for Thyroxine
This example is the same as Example 1 with the following exceptions:
In step 1, the solid body is coated with thyroxine-binding globulin (TBG) instead of gonorrhea antibody.
In step 3, fluorescent TBG is used or else a fluorescent antibody made against $T_4$ (instead of fluorescent antibody solution).
Step 5 then indicated thyroxine titre.

Example 3. The Indirect Technique for Gonorrhea
Steps:
1. Drop a 10 mm nylon ball into the cuvette. The ball has previously been coated with gonococcus antigen (dry film of the bacteria).
2. Add enough serum to cover the ball. Incubate at room temperature for 5 minutes, then pour off. If antibody to gonorrheal infection is present in the patient's serum, it will adhere to the coated ball.
3. Add fluorescent-tagged antihuman immunoglobulin (from rabbit or goat and commercially available from many sources). Incubate for 5 minutes, then pour off.
4. Rinse well with buffer solution, then pour off.
5. Place cuvette into the fluorometer and read the results.

Example 4. The Indirect Technique for other Bacteria
The technique of Example 3 is well adapted to assay of Toxiplasmosis, Streptococcus, and Staphylococcus infections and also to Treponemal (syphilis) infections using the appropriate antigen and antibody in each instance.

Example 5. Competitive Inhibition
Steps:
1. Drop a 10 mm diameter nylon ball coated with gonorrhea antibody into a first cuvette.
2. In a second cuvette, add 1 ml. of the subject's serum and 1 ml of a prepared fluorescent-tagged antigen solution. Mix together briefly and add contents to the first cuvette.
3. Incubate for 5 minutes at room temperature, pour off.
4. Rinse well with buffer solution, pour off.
5. Place cuvette into the fluorometer and read the results.

Note: In this Example, when the subject is antigen-free (infection free), all antibody binding sites on the nylon ball will be used to bind the tagged antigen, and therefore, give a maximum fluorescent signal.

The more antigen (infection) in the subject's serum the more competition for binding sites by non-fluorescent antigen molecules. Thus, the greater the titre, the greater reduction in fluorescent signal. This Example requires a different calibration curve, using known electronics circuitry and the lower the signal the greater the titre of infection.

Example 6.
This series of measurements illustrates the more than one-order-of-magnitude improvements in sensitivity of the system of this invention to a fluorescent substance on a solid surface over measurements made in two conventional fluorometers adapted for this purpose using their thin layer chromatography plate scanning attachments. The dye used was fluorescein isothiocyanate (FITC) diluted in pH 8.6 barbital buffer. A measureed amount of various dilutions was spotted on a polymethylmethacrylate surface and allowed to dry. The spots were excited at a wavelength of 480nm and their fluorescent emission read at a wavelength of 520nm. The following readings were obtained:

| Amount of FITC on Spot, Nanograms | Fluorescent Signal (normalized*) | | |
|---|---|---|---|
| | This System | Turner Model III | Aminco-Bowman |
| 0.01 | None | None | None |
| 0.04 | 0.4 | None | None |
| 0.16 | 3.2 | None | None |
| 0.64 | 17.7 | 5.3 | 1.4 |
| 2.5 | 55.6 | 24.2 | 37.4 |

-continued

| Amount of FITC on Spot, Nanograms | Fluorescent Signal (normalized*) | | |
|---|---|---|---|
| | This System | Turner Model III | Aminco-Bowman |
| 10.0 | 100.0 | 100.0 | 100.0 |

*Calculated as percent of signal from 10.0 nanograms after subtraction of blank reading.

The lower level of detectability achieved by this invention is due in large part to the 0.8 mm close proximity of the light input end of the fiber optics employed to the sample surface, and subsequent conservation of the light energy so captured. The Turner fluorometer is designed in a way that captures only that portion of emitted fluorescence that passes through a 0.2 × 2.0 cm slit 7 cm away and at an angle of 45° from the sample surface. The Aminco-Bowman fluorometer is designed so it captures a considerable portion of the emitted fluorescence in the light input end of an approximately ⅛-inch diameter fiber optic cable positioned closely to the sample, but it uses the fiber optic cable as an attachment to transmit the captured emission to a mirror positioned where a cuvette would normally be for observing liquid samples. The light reflected from this mirror radiates in three dimensions and only a small portion of it falls upon a 0.2 cm × 1 cm entry aperture, the first component in the further light conducting means, located approximately ¾-inch from the mirror. Because of the configuration of the above Turner and Aminco-Bowman fluorometers, calculations show that they fail to transmit more than 1% of the emitted light they pick up to the detector.

Example 7.

These measurements illustrate the importance of unhindered close proximity in attaining maximum fluorescent signal from a fluorecent substance on a solid surface. A ¼-inch diameter fiber optics bundle was used to measure a 6 mm diameter spot. The substance viewed is 1.0 microgram of fluorescein isothyiocyanate labeled goat anti-rabbit globulin diluted in pH 7.6 phosphate buffer spotted on an acid-etched polymethylmethacrylate surface and allowed to dry. Excitation and viewing is through randomly arranged fibers in a bifurcated fiber optic bundle. Excitation wavelength was 480 nm, measured emission wavelength was 520 nm. The following readings were obtained:

| Distance of End of Bundle from Surface, millimeters | Fluorescent Signal, % of Maximum |
|---|---|
| 0.8 | 100.0 |
| 1.0 | 100.0 |
| 2.0 | 81.1 |
| 3.0 | 54.1 |
| 4.0 | 39.2 |
| 6.0 | 14.6 |
| 12.5 | 3.4 |

Example 8.

This example illustrates a fluorescent measurement of an antibody-antigen reaction in which an antigen in solution is fluorescently labeled and reacted with an antibody immobilized on a surface. In this so-called "direct" technique, the fluorescence of the surface is proportional to the antigen concentration in solution.

Polyamide strips were coated with Anti-streptolysin 0 by immersing them for 30 minutes in a slowly stirred solution of Anti-Streptolysin 0 diluted 1:8 in saline solution while 1% glutaraldehyde was slowly added. After water washing and drying the strips were exposed to various concentrations of Streptolysin 0 Toxin is distilled water. Two ml of each concentration were first reacted with 0.2 ml of fluorescamine solution (40 mg in 100 ml acetone) to affect labeling of the antigen. The strips were then added and stirred for 30 minutes, removed, water rinsed, and allowed to dry. They were then placed in the instrument, excited at a wavelength of 375 nm and fluorescence measured at a wavelength of 475 nm. The following results were obtained:

| Streptolysin O Toxin Dilution | Fluorescent Signal |
|---|---|
| 1:5 | 280 |
| 1:10 | 155 |
| 1:20 | 105 |
| 1:40 | 45 |
| 1:1000 | 5 |
| Blank | 0 |

Example 9.

This example illustrates a fluorescent measurement of bacteria in which bacteria in suspension are bound to a surface and reacted with fluorescently labeled antibody, in a so-called sandwich technique. The fluorescence of the surface is proportional to the bacterial concentration of the sample.

A pure culture of Streptococcus beta-hemolyticus Type A was grown in trypsin broth, autoclaved, centrifuged and washed with phosphate buffered saline (PBS). The cells were resuspended in PBS to concentrations of $10^7$, $10^5$, and $10^3$ organisms per ml.

DEAE-cellulose strips were coated with Streptococcus A Antiserum by immersing them for 15 minutes in a stirred solution of antiserum diluted 1:16 in phosphate buffer while 0.5 ml of 50% glutaraldehyde was slowly added. After washing, individual strips were incubated for 5 minutes in 5 ml of each of the concentrations mentioned above, followed by washing with PBS.

Next, the strips were incubated for 5 minutes in a solution fluorescein isothiocyanate labeled Streptococcus A antibody diluted 1:4 in phosphate buffer, rinsed with buffer, and air dried. The strips were then placed in the instrument and the following readings were obtained:

| Streptococcal Concentration Organisms per ml. | Fluorescent Signal |
|---|---|
| $10^7$ | 840 |
| $10^5$ | 305 |
| $10^3$ | 122 |

Example 10.

This example describes the fluorescent measurement of multiple surfaces that have been exposed to a common solution containing several substances for which measurement is desired.

Four squares of cellulose each containing a different covalently bonded immunoglobulin antibody (goat anti-human IgA, IgE, IgG and IgM) and mounted on a plastic strip are placed in a sample of serum diluted in suitable buffer. After incubation for two hours, the strip is removed and the four coated squares rinsed with buffer. They are then reacted with a solution containing equally active concentrations of fluorescein isothiocyanate labeled goat anti-human IgA, IgE, IgG and IgM diluted in suitable buffer and allowed to incubate another two hours. The strips are again washed, allowed to air dry, and each area is separately read in the instrument. The relative concentrations of the various immunoglobulins are so determined.

Example 11.

This example describes the fluorescent measurement of a common surface exposed to a solution containing several substances for which individual measurements are desired.

A circular disc of polymethylmethacrylic acid containing a random mixture of three different covalently bonded anti-drug antibodies (rabbit anti-morphine, anti-cocaine, and anti-barbiturate), mounted on a strip of polymethylmethacrylate, is exposed to a sample of urine diluted in suitable buffer. After incubation for one hour, the strip is removed and the disc rinsed with buffer. It is then incubated in a solution containing a mixture of rabit antibodies to these drugs, each antibody labeled with a different fluorochrome, i.e., fluorescamine labeled rabbit anti-morphine, fluoroscein isothiocyanate labeled rabbit anti-cocaine, and lissamine rhodamine B200 labeled rabbit anti-barbiturate, diluted in suitable buffer and incubated two hours. The strip is removed, washed with buffer, and allowed to dry. It is then read sequentially in the instrument exciting first at 390 nm and reading emission at 485 nm, then at 480 and 520 nm, respectively, and finally at 520 and 595 nm, respectively. The presence of morphine, cocaine or barbiturate are so determined.

It will be understood that the above specific description and drawings have been given for the purposes of illustration only and that variations and modifications can be made therein without departing from the spirit and scope of the appended claims.

To those skilled in the art to which this invention relates, many changes in construction and widely differing embodiments and applications of the invention will suggest themselves without departing from the spirit and scope of the invention. The disclosures and the description herein are purely illustrative and are not intended to be in any sense limiting.

What is claimed is:

1. In a body adapted to enable fluorometric detection and determination of at least two different sample substances, first and second sample substances carried by a surface of said body in immobilized form and in random dispersion, each sample substance being immunologically bound to a prelabelled fluorescent substance selectively reactive with it, respective fluorescent substances being distinguishable from one another by differences in their fluorescent behavior.

2. A body as in claim 1 in which said sample substance comprises antigen and said prelabelled fluorescent substance comprises a fluorescently labeled antibody.

3. A body as in claim 1 in which said sample substance comprises antibody and said prelabelled fluorescent substance comprises a fluorescently labelled antigen.

4. A body adapted to enable fluorometric detection and determination of at least two different antigens or antibodies, said body comprising a substrate having at least first and second different coating areas spaced from each other, first and second sample antigen or antibody carried by said first and second coating areas, respecively, in immobilized form, specific first antigen or antibody immunologically bound to said first antigen or anitbody and prelabelled with a first fluorescent substance, specific second antigen or antibody immunologically bound to said second sample antigen or antibody and prelabelled with a second fluorescent substance, said labelled first and second antigen or antibody being monospecific for said first and second sample antigens or antibodies, the intensity of fluorescence emitted from said coating areas being proportional to the quantity of labelled antigen or antibody on said surface.

5. A body as in claim 4 in which said coating areas comprise bands.

6. A body as in claim 4 in which said first and second fluorescent substances emit fluorescence at different wavelengths.

7. A body adapted to enable fluorometric detection and determination of at least one antigen or antibody, said body comprising a substance having at least two different coating areas spaced from each other, a sample antigen or antibody carried by one coating area, a specific first antigen or antibody immunologically bound to said first antigen or antibody and prelabelled with a fluorescent substance, another coating area comprising a standard coating area carrying a predetermined quantity of standard antigen or antibody of said sample type, specific antigen or antibody immunologically bound to said standard antigen or antibody and prelabelled with a fluorescent substance, the intensity of fluorescence emitted from said coating areas being proportional to the quantity of labelled antigen or antibody on said surface.

8. A polyhedron body adapted to enable detection and determination of more than one fluorescent sample substance including a material derived from a biological fluid or tissue, said body comprising a substrate having multiple different coating areas perminently bound to selected faces of said polyhedron and spaced from each other, each such coating area being coated with different ones of said substances.

* * * * *